(12) United States Patent
Valuck et al.

(10) Patent No.: US 11,640,857 B2
(45) Date of Patent: May 2, 2023

(54) TECHNIQUES FOR PROVIDING REFERRALS FOR OPIOID USE DISORDER TREATMENT

(71) Applicant: RxAssurance Corporation, Denver, CO (US)

(72) Inventors: Robert J. Valuck, Denver, CO (US); Thomas C. Ennis, Denver, CO (US)

(73) Assignee: RXASSURANCE CORPORATION, Denver, CO (US)

( * ) Notice: Subject to any disclaimer, the term of this patent is extended or adjusted under 35 U.S.C. 154(b) by 328 days.

(21) Appl. No.: 16/985,963

(22) Filed: Aug. 5, 2020

(65) Prior Publication Data

US 2021/0043310 A1 Feb. 11, 2021

Related U.S. Application Data

(60) Provisional application No. 62/882,893, filed on Aug. 5, 2019.

(51) Int. Cl.
| | | |
|---|---|---|
| *G16H 40/20* | (2018.01) | |
| *G06Q 30/00* | (2012.01) | |
| *G06F 16/29* | (2019.01) | |
| *G16H 10/60* | (2018.01) | |
| *G06Q 30/018* | (2023.01) | |
| *G16H 50/70* | (2018.01) | |
| *G06F 16/9537* | (2019.01) | |
| *G06F 16/23* | (2019.01) | |

(Continued)

(52) U.S. Cl.
CPC ........... *G16H 40/20* (2018.01); *A61B 5/4848* (2013.01); *G06F 16/2379* (2019.01); *G06F 16/29* (2019.01); *G06F 16/9537* (2019.01); *G06Q 30/018* (2013.01); *G06Q 30/0282* (2013.01); *G16H 10/60* (2018.01); *G16H 50/70* (2018.01); *G06Q 40/08* (2013.01)

(58) Field of Classification Search
CPC ........ G16H 40/20; G16H 10/60; G16H 50/70; A61B 5/4848; A61B 5/0022; A61B 5/165; A61B 5/4845; A61B 5/7275; G06F 16/2379; G06F 16/29; G06F 16/9537; G06Q 30/018; G06Q 30/0282; G06Q 40/08

See application file for complete search history.

(56) References Cited

U.S. PATENT DOCUMENTS

| | | | |
|---|---|---|---|
| 2017/0193171 A1* | 7/2017 | Perroth ................. | G16H 40/20 |
| 2020/0019946 A1* | 1/2020 | Walker .................. | G06Q 20/14 |

\* cited by examiner

*Primary Examiner* — Maroun P Kanaan

(74) *Attorney, Agent, or Firm* — ArentFox Schiff LLP

(57) ABSTRACT

Examples described herein generally relate to referring a patient to a provider for a drug use disorder. A computer system accesses a plurality of provider data records. The system determines a geographical location of the patient. The system searches, within a geographical distance of the geographical location for a provider that satisfies patient requirements based on a patient data record. The system determines one or more certified providers that are certified to treat a condition of the patient. The system determines that one or more of the certified providers has an available opening for the patient. The system determines an outcome rating for the patient and each certified provider based on the patient data record. The system matches the patient to a certified provider with a best outcome rating that accepts payment from a payer for the patient. The system refers the patient to the matched provider.

11 Claims, 9 Drawing Sheets

(51) Int. Cl.
*A61B 5/00* (2006.01)
*G06Q 30/0282* (2023.01)
*G06Q 40/08* (2012.01)

FIG. 6

TreatmentGPS

Dashboard | 🔵 Chris Ennis ▾

Provider: Denver Family Therapy Center

| Provider Details | Treatment Details | Notes | Change Log | Referrals |

Care Type

- Payment Types
- Facility Type
- Treatment Approach
- Service Setting
- Organization Type
- Licensing / Accreditation
- Age Coverage
- Gender Coverage Care Type

- ☐ Acamprosate (Camprat)
- ☑ Accepts clients on opioid medication
- ☐ All Clients in Opioid Treatment Program
- ☐ Buprenorphine detoxification
- ☐ Buprenorphine maintenance
- ☐ Buprenorphine maintenance for predetermined time
- ☐ Buprenorphine used in treatment
- ☐ Detoxification
- ☐ Disulfram (Antabuse)
- ☐ Do not treat opioid addiction
- ☐ Do not use medication for opioid addiction
- ☐ Medications for psychiatric disorders

- ☐ Methadone
- ☐ Methadone detoxification
- ☐ Methadone maintenance
- ☐ Methadone maintenance for predetermined time
- ☐ Naltrexone (oral)
- ☐ Prescribes/administer buprenorphine and/or naltrexone
- ☐ Relapse prevention from naltrexone
- ☐ SAMSHA-certified Opioid Treatment Program
- ☑ Substance abuse treatment
- ☐ Transitional housing or halfway house
- ☐ Use methadone/buprenorphine for pain management or emergency dosing
- ☐ Vivitrol (injectable Naltrexone)

[Update Listing]

600
610
620
630

TECHNIQUES FOR PROVIDING REFERRALS FOR OPIOID USE DISORDER TREATMENT

CLAIM OF PRIORITY UNDER 35 U.S.C. § 119

This application claims priority to U.S. Provisional Application No. 62/882,893 titled "TECHNIQUES FOR PROVIDING REFERRALS FOR OPIOID USE DISORDER TREATMENT," filed Aug. 5, 2019, which is assigned to the assignee hereof, and incorporated herein by reference in its entirety.

BACKGROUND

The present disclosure relates to decision support for doctors, and particularly to recommendations for therapeutic treatment protocols for pharmacological administration.

70,237 drug overdose deaths occurred in the United States in 2017. The age-adjusted rate of overdose deaths increased significantly by 9.6% from 2016 (19.8 per 100,000) to 2017 (21.7 per 100,000). Opioids—mainly synthetic opioids (other than methadone)—are currently the main driver of drug overdose deaths. Opioids were involved in 47,600 overdose deaths in 2017 (67.8% of all drug overdose deaths). Addiction to opioids (clinically referred to as Opioid Use Disorder, or OUD) is more common than previously thought, and affects between 1-5% of the U.S. population. Opioid prescribing comprises 9% of all prescribing in the U.S., and most individuals who become addicted or overdose began with prescribed opioids.

Finding treatment for a patient with OUD may be difficult. Although OUD treatment may be covered by various payers including Medicaid, Medicare, and private insurance, medical providers may provide only certain types of treatments or may only accept payment from specific payers. Accordingly, resources for OUD treatment are often limited.

Thus, there is a need in the art for improvements in providing referrals for treatment of OUD. In particular, there is a need for systems and methods for matching patients to available providers.

SUMMARY

The following presents a simplified summary of one or more implementations of the present disclosure in order to provide a basic understanding of such implementations. This summary is not an extensive overview of all contemplated implementations and is intended to neither identify key or critical elements of all implementations nor delineate the scope of any or all implementations. Its sole purpose is to present some concepts of one or more implementations of the present disclosure in a simplified form as a prelude to the more detailed description that is presented later.

In an example, the disclosure provides a method of treating a patient for a substance use disorder. The method may include accessing a plurality of provider data records by periodically accessing corresponding data sources and rectifying records based on an accuracy rating of each data source. The method may include determining a geographical location of the patient. The method may include searching, within a geographical distance of the geographical location for a provider of treatment that satisfies patient requirements based on a patient data record, wherein the searching includes. The method may include determining one or more certified providers that are certified to treat a condition of the patient. The method may include determining that one or more of the certified providers has an available opening for the patient. The method may include determining an outcome rating for the patient and each certified provider based on the patient data record. The method may include matching the patient to a certified provider with a best outcome rating that accepts payment from a payer for the patient. The method may include referring the patient to the matched provider.

In another aspect, the disclosure provides a system for treating a patient for a substance use disorder. The system may include a memory storing computer-executable instructions and a processor configured to execute the computer-executable instructions. The processor may access a plurality of provider data records by periodically accessing corresponding data sources and rectifying records based on an accuracy rating of each data source. The processor may determine a geographical location of the patient. The processor may searching, within a geographical distance of the geographical location for a provider of treatment that satisfies patient requirements based on a patient data record. The processor may determine one or more certified providers that are certified to treat a condition of the patient. The processor may determine that one or more of the certified providers has an available opening for the patient. The processor may determine an outcome rating for the patient and each certified provider based on the patient data record. The processor may match the patient to a certified provider with a best outcome rating that accepts payment from a payer for the patient. The processor may refer the patient to the matched provider.

In another aspect, the disclosure provides a non-transitory computer readable medium storing computer-executable instruction. The non-transitory computer readable medium may include instructions to access a plurality of provider data records by periodically accessing corresponding data sources and rectifying records based on an accuracy rating of each data source. The non-transitory computer readable medium may include instructions to determine a geographical location of the patient. The non-transitory computer readable medium may include instructions to search, within a geographical distance of the geographical location for a provider of treatment that satisfies patient requirements based on a patient data record. The non-transitory computer readable medium may include instructions to determine one or more certified providers that are certified to treat a condition of the patient. The non-transitory computer readable medium may include instructions to determine that one or more of the certified providers has an available opening for the patient. The non-transitory computer readable medium may include instructions to determine an outcome rating for the patient and each certified provider based on the patient data record. The non-transitory computer readable medium may include instructions to match the patient to a certified provider with a best outcome rating that accepts payment from a payer for the patient. The non-transitory computer readable medium may include instructions to refer the patient to the matched provider.

Additional advantages and novel features relating to implementations of the present disclosure will be set forth in part in the description that follows, and in part will become more apparent to those skilled in the art upon examination of the following or upon learning by practice thereof.

DESCRIPTION OF THE FIGURES

In the drawings:

FIG. 6 illustrates an example provider interface, in accordance with an implementation of the present disclosure.

DETAILED DESCRIPTION

Figure 1:
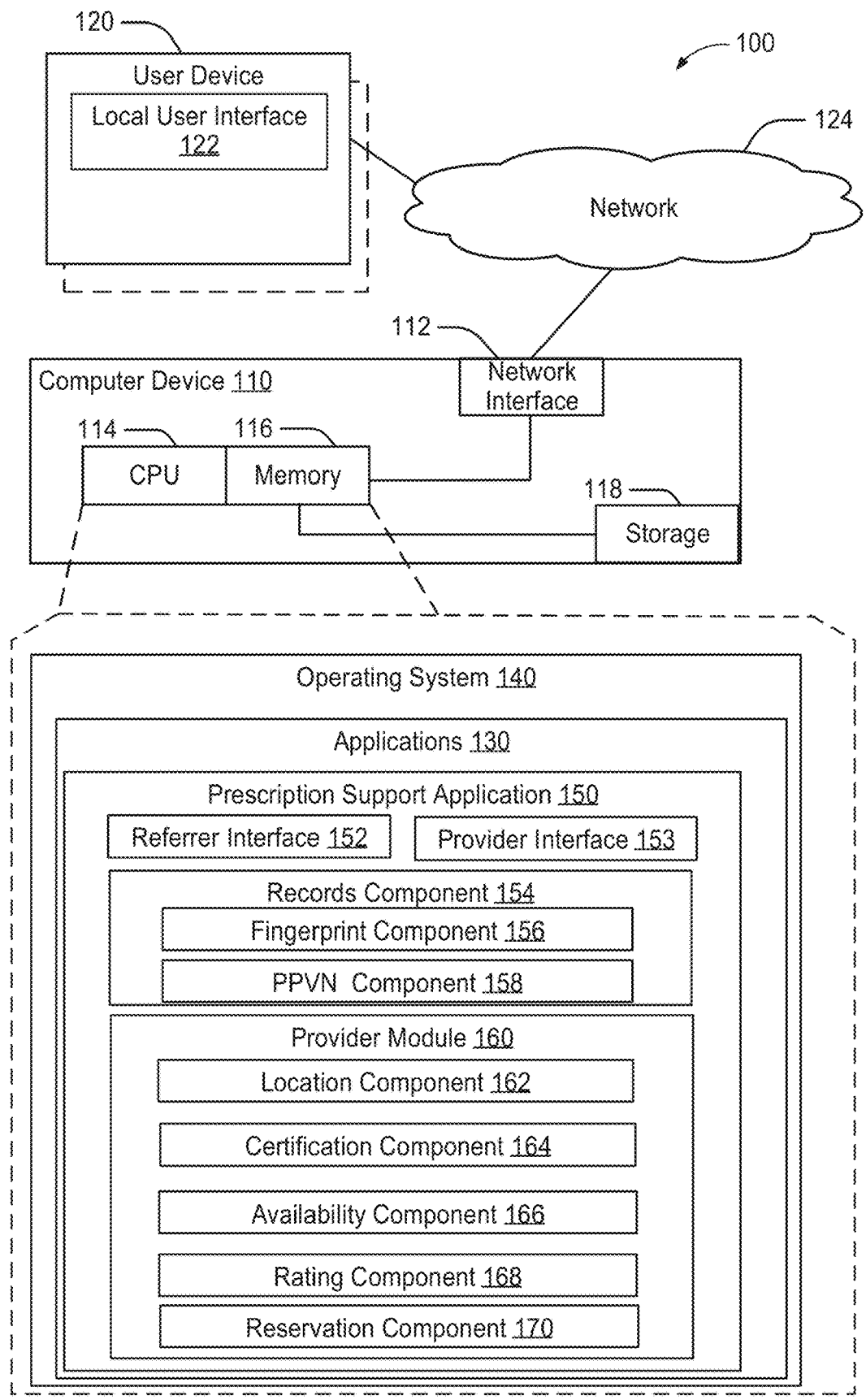
FIG. 1 is a diagram of an example computer system for providing referrals to providers for opioid use disorder, in accordance with an implementation of the present disclosure.

The present disclosure provides systems and methods for referring a patient with a substance use disorder to a health care provider who can provide appropriate treatment, as well as methods for treating a patient with a substance use disorder by directing them to appropriate healthcare providers who can provide treatment. The disclosure provides techniques that allow a computer system to facilitate referral of a patient to an appropriate health care provider (e.g., a treatment center) having availability to treat a condition of the patient, which condition may be a substance use disorder. In one aspect of the invention, the substance use disorder may be an opioid use disorder. Opioid Use Disorder is a diagnosis introduced in the fifth edition of the Diagnostic and Statistical Manual of Mental Disorders, DSM-5. It combines two disorders from the previous edition of the Diagnostic and Statistical Manual, the DSM-IV-TR, known as Opioid Dependence and Opioid Abuse, and includes a wide range of illicit and prescribed drugs of the opioid class. Although the generic term, Opioid Use Disorder, is given in the DSM-5, the guidelines indicate that the actual opioid drug being used by the individual is specified in the diagnosis.

Treatment centers for substance use disorders may require certifications to provide specific treatments. For instance, for patients with opioid use disorders, administering or supplying alternative opioids such as naltrexone or methadone may require an X waiver due to controls on the alternative opioids. Facilities with appropriate certifications may have limited numbers of beds or spaces for accepting new patients.

In an aspect, a patient with a drug use disorder, or a healthcare provider treating that patient, may require assistance in finding an appropriate facility. For example, first responders responding to a case of a drug overdose or other opioid related incident may encounter an incapacitated patient or patient with diminished or impaired capacity. The first responder may be faced with a choice of finding a treatment center for the patient or taking the patient to jail. Even if the first responder can find an available treatment center, securing a bed for the patient may be difficult due to unavailability of patient records and consent for transferring such records. Family members and even other health care professionals assisting a patient may face similar issues.

In an aspect, the present disclosure provides a system that may be utilized by a patient, health care provider, or other third party to provide a referral for the patient to a health care facility that can treat a condition of the patient. The condition may be a substance use disorder such as OUD, but may also be a condition such as behavioral health, anxiety, sleep, or depression, which may be considered comorbidities, but may not involve a diagnosis of OUD. The system may periodically access a plurality of provider data records to update information regarding providers. The referral may be based on a geographic location of the patient. The system may search within a geographical distance of the geographical location of the patient for a provider that satisfies patient requirements based on a patient data record. For example, the system may determine one or more certified providers that are certified to treat a condition of the patient. The system may determine whether each of the certified provides has an opening for the patient. The system may determine an outcome rating for the patient and each certified provider based on the patient data record. The system may match the patient to a certified provider with the best outcome rating that accepts payment from a payer for the patient. The system may refer the patient to the matched provider. In an aspect, referring the patient to the matched provider may include transferring a patient record to the matched provider using a patient portable virtual network that tracks a consent of the patient and the patient record in a blockchain. The system may also electronically reserve the available opening using the patient portable virtual network to transfer patient information.

Referring now to FIG. 1, an example referral system 100 includes a central computer device 110 and a plurality of user devices 120. The central computer device 110 may be, for example, any mobile or fixed computer device including but not limited to a computer server, desktop or laptop or tablet computer, a cellular telephone, a personal digital assistant (PDA), a handheld device, any other computer device having wired and/or wireless connection capability with one or more other devices, or any other type of computerized device capable of processing pharmacological related data. In an aspect, the central computer device 110 may be implemented as one or more virtual machines hosted by a web services provider.

The computer device 110 may include a central processing unit (CPU) 114 that executes instructions stored in memory 116. For example, the CPU 114 may execute an operating system 140 and one or more applications 130, which may include a referral application 150. The computer device 110 may also include a network interface 112 for communication with external devices via a network 124. For example, the computer device 110 may communicate with a plurality of user devices 120.

Memory 116 may be configured for storing data and/or computer-executable instructions defining and/or associated with an operating system 140 and/or application 130, and CPU 114 may execute operating system 140 and/or application 130. Memory 116 may represent one or more hardware memory devices accessible to computer device 110. An example of memory 116 can include, but is not limited to, a type of memory usable by a computer, such as random access memory (RAM), read only memory (ROM), tapes, magnetic discs, optical discs, volatile memory, non-volatile memory, and any combination thereof. Memory 116 may store local versions of applications being executed by CPU 114. In an implementation, the memory 116 may include a storage device 118, which may be a non-volatile memory.

In an aspect, the storage device 118 may include a blockchain storage. The blockchain storage may store immutable records by allowing append operations only such that the records are sequenced. Further, the records may use hash chaining such that each record may be cryptographically verified to provide data security. In an implementation, the blockchain storage may be distributed or duplicated across devices. In an aspect, the blockchain storage may be utilized for smart contracts. For example, a patient consent record may be stored in the blockchain storage and verified when records for the patient are accessed.

The CPU 114 may include one or more processors for executing instructions. An example of CPU 114 can include, but is not limited to, any processor specially programmed as described herein, including a controller, microcontroller, application specific integrated circuit (ASIC), field programmable gate array (FPGA), system on chip (SoC), or other programmable logic or state machine. The CPU 114 may include other processing components such as an arithmetic logic unit (ALU), registers, and a control unit. The CPU 114 may include multiple cores and may be able to process different sets of instructions and/or data concurrently using the multiple cores to execute multiple threads. In an aspect, a graphics processing unit (GPU) may perform some operations of the CPU 114. For example, for blockchain operations, a GPU may be utilized for mining blocks (e.g., finding hash keys).

The operating system 140 may include instructions (such as applications 130) stored in memory 116 and executable by the CPU 114. The applications 130 may include a referral application 150 executed by the computer device 110. The referral application 150 may generate a referral for the patient to a provider based on a patient record and records of providers within a geographical area. The referral application 150 may include a referrer interface 152 that receives input from a patient, referring health care provider, or other third party, a provider interface 153 that allows a health care provider to update a provider record, a records component 154 that accesses a plurality of data records associated with the patient and providers; and a provider module 160 that matches the patient to an available certified provider for a condition of the patient.

The referral application 150 may include a referrer interface 152 that may be in communication with or otherwise operate in conjunction with a local user interface 122 on a user device 120. The referrer interface 152 may be any user interface with which an end user may interact. For example, the referrer interface 152 may be an application or operating system that runs on the user devices 120. The referral application 150 may be associated or in communication with an online store or update service. Accordingly, the referral application 150 may occasionally publish an updated version of the referrer interface 152 to the local user interface 122. As another example, the referrer interface 152 may be a web-page that is accessed through a browser application executed on the user devices 120. By loading the web-page, the browser application may effectively operate as a user interface for an application executed on the computer device 110 (e.g., in the case of a web server).

In an aspect, the referrer interface 152 may present a search tool for finding a provider. The referrer interface 152 may identify the patient, for example, using an account or an entered patient identifier. The referrer interface 152 may include fields for entering information that may not be stored in a patient record. For example, the referrer interface 152 may include a field for entering a patient location. Alternatively, the patient location may be determined based on a GPS location of a user device 120. In another example, the referrer interface 152 may collect patient data that may be accessed and recorded from a wearable. The patient data may include biometric vital signs, including, but not limited to heart rate, heart rate variability, blood pressure, respiration, and temperature. Such patient data may be used to calculate or update clinically diagnosed conditions including, but not limited to pain, function, anxiety, depression, and sleep. The referrer interface 152 may display information for available providers as a map and/or list. The referrer interface 152 may receive an input from a user selecting a provider. The referrer interface 152 may provide additional information and/or options for generating a referral in response to the selection of a provider.

In an aspect, the referrer interface 152 may provide control over a patient private virtual network (PPVN). The PPVN may store a patient record and a consent document in a blockchain storage. The patient may remotely access the PPVN to share the patient record with a health care provider. In an aspect, the referral system 100 may request the patient to provide consent to sharing of the patient record via the PPVN before making a referral or reserving an opening at a provider.

The provider interface 153 may include the same functionality as the referrer interface 152 for the provider to enter information on behalf of a patient. The provider interface 153 may also provide tools for updating provider information. For example, the provider interface 153 may allow the provider to view a current provider record and update one or more elements of the record. For instance, a provider may update the record as new treatments become available or certifications are obtained. In an aspect, the provider interface 153 may also be used to notify a provider of a referral and/or a reservation. For example, the provider interface 153 may provide patient information to the health care provider before the patient arrives at the provider. In an aspect, the provider interface 153 may allow the provider to request consent for obtaining a patient record.

The referral application 150 may include a records component 154. The records component 154 may access a plurality of data records for a patient, provider, payer, or drug. The records component 154 may correlate and rectifying the records based on an accuracy rating of each data source. For example, an electronic health record (EHR) may be considered a highest level of truth, but may be supplemented with information from other sources such as a state prescription drug monitoring program (PDMP), electronic patient reported outcome (ePRO), toxicology lab test results, medical and pharmacy claims, medication history, FDA drug information (including the FDA-approved prescribing information for drug products), or health insurance information.

In an aspect, the referral application 150 and/or the records component 154 may include a fingerprint component 156 that generates a data fingerprint of collected data records for a recommendation. The system generated data 'fingerprint' may include auditable metadata and data keys, including, but not limited to, API's, transactions, permissions, and timestamped information of all relevant data accessed and used in any manner to create and deliver clinical decision support recommendations. The fingerprint component 156 may generate a fingerprint for each set of data records provided to the provider module 160.

The records component 154 may include a PPVN component 158 that manages a patient PPVN. For example, the PPVN component 158 may perform blockchain operations for updating the PPVN based on patient actions. For instance, the PPVN component 158 may add a new block when the patient provides a new consent form, revokes a consent form, or is admitted to a treatment center.

The provider module 160 may match a patient to a provider that can provide treatment that satisfies patient requirements. The provider module 160 may search within a geographical distance of the geographical location of the patient for matching providers. The provider module 160 may include a location component 162 that determines providers within a geographical area, a certification component 164 that determines which providers are certified to treat a condition of the patient, an availability component that determines which providers have available openings for the patient, a rating component that estimates a success rating for each provider, and a reservation component that reserves an opening at a matched provider.

The location component 162 may determine providers within a geographical area based on a geographical location of the patient and a geographical distance. As discussed above, the geographical location may be received via the referrer interface 152. The geographical distance may be a radius from the geographical location of the patient that defines a circular geographic area. In another aspect, the geographical distance may be a travel time of the patient using one or more indicated method of travel (e.g., walking, public transportation, or private vehicle). Accordingly, the location component 162 may determine providers that are physically accessible to the patient.

The certification component 164 may determine one or more certified providers that are certified to treat a condition of the patient. The certification component 164 may determine the condition of the patient based on the patient medical record from the PPVN. The certification component 164 may determine whether any controlled drugs are required to treat the condition of the patient and determine which certifications are required for the controlled drugs. For example, controlled drugs may be classified as schedule III, IV, or V narcotics and may include buprenorphine, naltrexone, or methadone, for example. The certification component 164 may compare the required certifications to certifications of provider records to determine a set of certified providers.

The availability component 166 may determine whether each provider in the set of certified providers has an available bed or opening for the patient. In an aspect, the availability component 166 may determine a number of available openings at a provider based on the provider record. In an aspect, the availability component 166 may query a provider system to determine whether an indicated number of available openings is still correct. The availability component 166 may also determine whether and how a bed may be reserved. For example, the availability component 166 may extract contact information, hours, location, electronic booking requirements, if available, and open walk in times from a provider record. In an aspect, when one or more providers indicate that there is no available opening, the availability component 166 may estimate when an opening is likely to become available based on a number of beds at the provider, referral criteria, and a length of a waiting list.

The rating component 168 may determine an outcome rating for the patient for each certified provider based on the patient data record. In an aspect, the rating component 168 may determine one or more matrices for rating a provider for a patient. For example, a provider match matrix may rate a provider based on patient background and receiving provider success rates by patient profile or receiving provider success rates with referral provider by patient profile. The rating component 168 may determine the outcome rating based on the success rate for the receiving provider for patients matching the patient background. In another aspect, a patient demographic matrix may include age, sex, ethnicity, patient profile, and treatment conditions. The rating component 168 may compare a patient demographic matrix of the provider to the patient to determine whether the provider has treated similar patients.

In an aspect, the rating component 168 may utilize one or more machine learning algorithms. As used herein, the term machine-learning algorithm may refer to executable code that is executed by a computer processor to process one or more elements of a data record and produce a defined result. A machine-learning algorithm may include a machine-learning model that is trained to produce the defined result. For example, the machine-learning model may include various operations and state information that reflects training of the model. Example machine-learning algorithms may include supervised learning, unsupervised learning, reinforcement learning, feature learning, sparse dictionary learning, anomaly detection, and association rules. Example models may include artificial or digital neural networks, decision trees, support vector machines, Bayesian networks, and genetic algorithms.

The reservation component 170 may reserve an available opening for a patient at a matched provider. Generally, because a reservation at a provider may include personally identifiable information and an indicated health condition, the reservation may be considered protected health information and may require consent of the patient. The reservation component 170 may determine whether the patient has consented to information sharing based on the PPVN. In an aspect, where an applicable consent form is not available, the reservation component 170 may facilitate obtaining consent. For example, the reservation component 170 may provide a consent form to the patient via the referrer interface 152. When the patient has consented to information sharing, the reservation component 170 may utilize the PPVN to transfer patient information to the provider.

Figure 2:
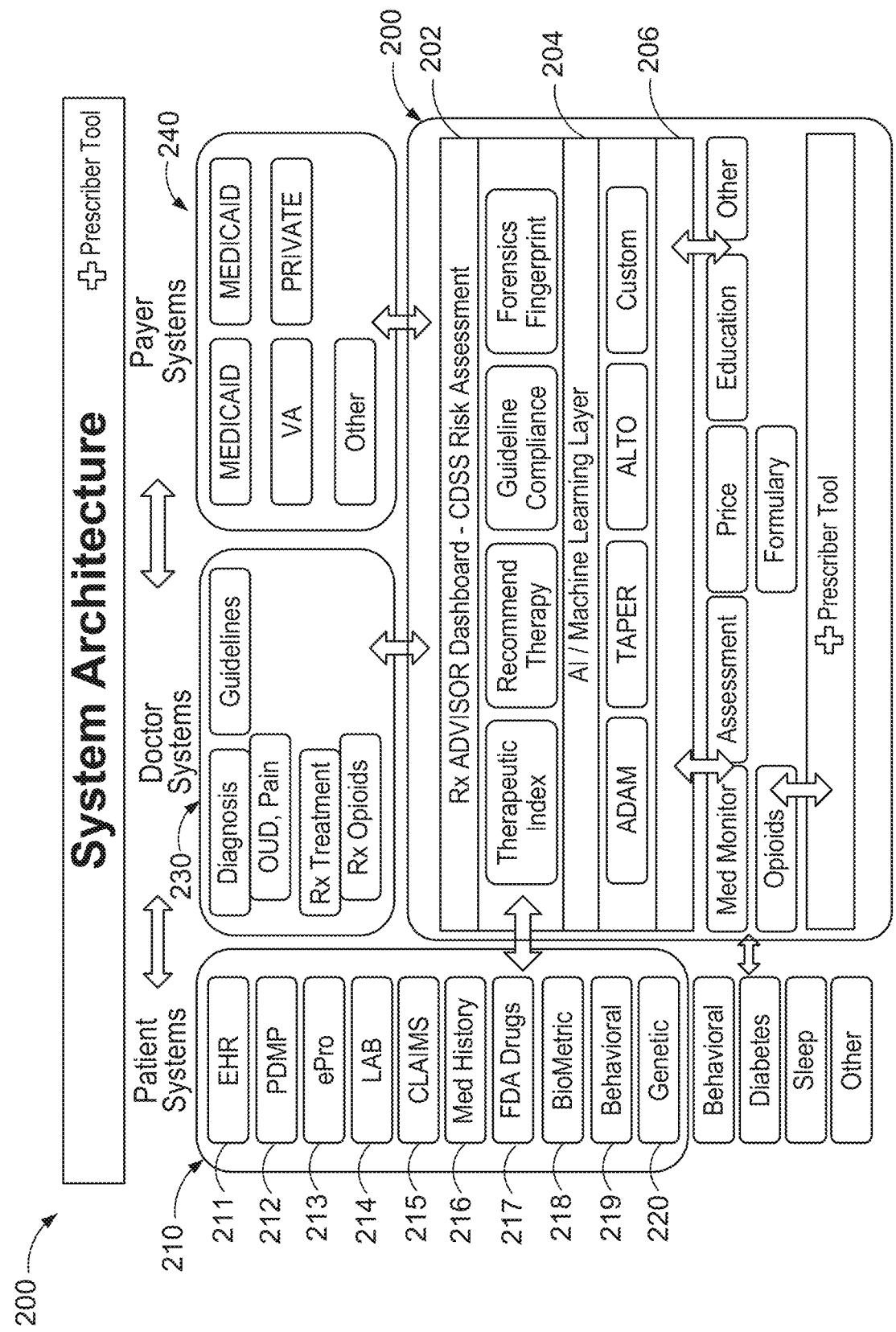
FIG. 2 is a diagram illustrating an example system architecture, in accordance with an implementation of the present disclosure.

FIG. 2 illustrates an example system architecture showing interaction and data transfer between an example pharmacological evaluation system 200, patient systems 210, a doctor system 230, and payer systems 240.

The pharmacological evaluation system 200 may be an example system for implementing the referral system 100. The pharmacological evaluation system 200 may include a prescription advisory dashboard 202 that provides clinical decision support services for risk assessment. The prescription advisory dashboard 202 may be an example of the provider interface 153 and may provide a therapeutic index, recommended therapy, and guideline compliance for data records indicated by a forensics fingerprint. The pharmacological evaluation system 200 may include an AI/Machine Learning layer 204 that may be used to implement the rating component 168, for example. In an aspect, the AI/Machine Learning layer 204 may include one or more of an automated drug advice and monitoring (ADAM) system, a drug taper system (TAPER), an alternative to opioids (ALTO) system, and custom algorithms that may implement the rating component 168. The pharmacological evaluation system 200 may include an API layer that interacts with other systems to acquire data and/or perform specific analysis. For example, the pharmacological evaluation system 200 may utilize an external system to track drug prices and access such a system via the API layer 206. Other services that may be accessed via an API include a medication monitoring system (e.g., for opioids), an assessment system, an education system, and a formulary.

The patient systems 210 may include any system that provides information about a patient. For example, the patient systems 210 may include an electronic health record (EHR) 211, a state prescription drug monitoring program (PDMP) 212, electronic patient reported outcome (ePRO) 213, toxicology lab test results 214, medical and pharmacy claims 215, and medication history 216. In an aspect the patient systems 210 may include access to FDA drug information 217 corresponding to drugs associated with the patient or being considered for the patient. The patient systems 210 may also include information such as biometric information 218, behavioral information 219, and genetic information 220. The behavioral information 219 may include patient reported data from standardized assessment scales for clinically diagnosed conditions including, but not limited to pain, function, anxiety, depression, sleep, as recorded on scales such as PEG-3, GAD-7, PHQ-9, SOWS, COWS, etc.

The doctor systems 230 may include information provided by a health care provider. The doctor systems 230 may include a diagnosis, which may indicate opioid use disorder and/or pain, for example. The doctor systems 230 may include a prescribed treatment, which may include prescription opioids. The doctor systems 230 may include guidelines, which may define acceptable treatments for the patient.

The payer systems 240 may include any system for a payer. Example payer systems include a Medicaid system, Medicare system, veterans affairs (VA) system, private insurance, and other payers.

Figure 3:
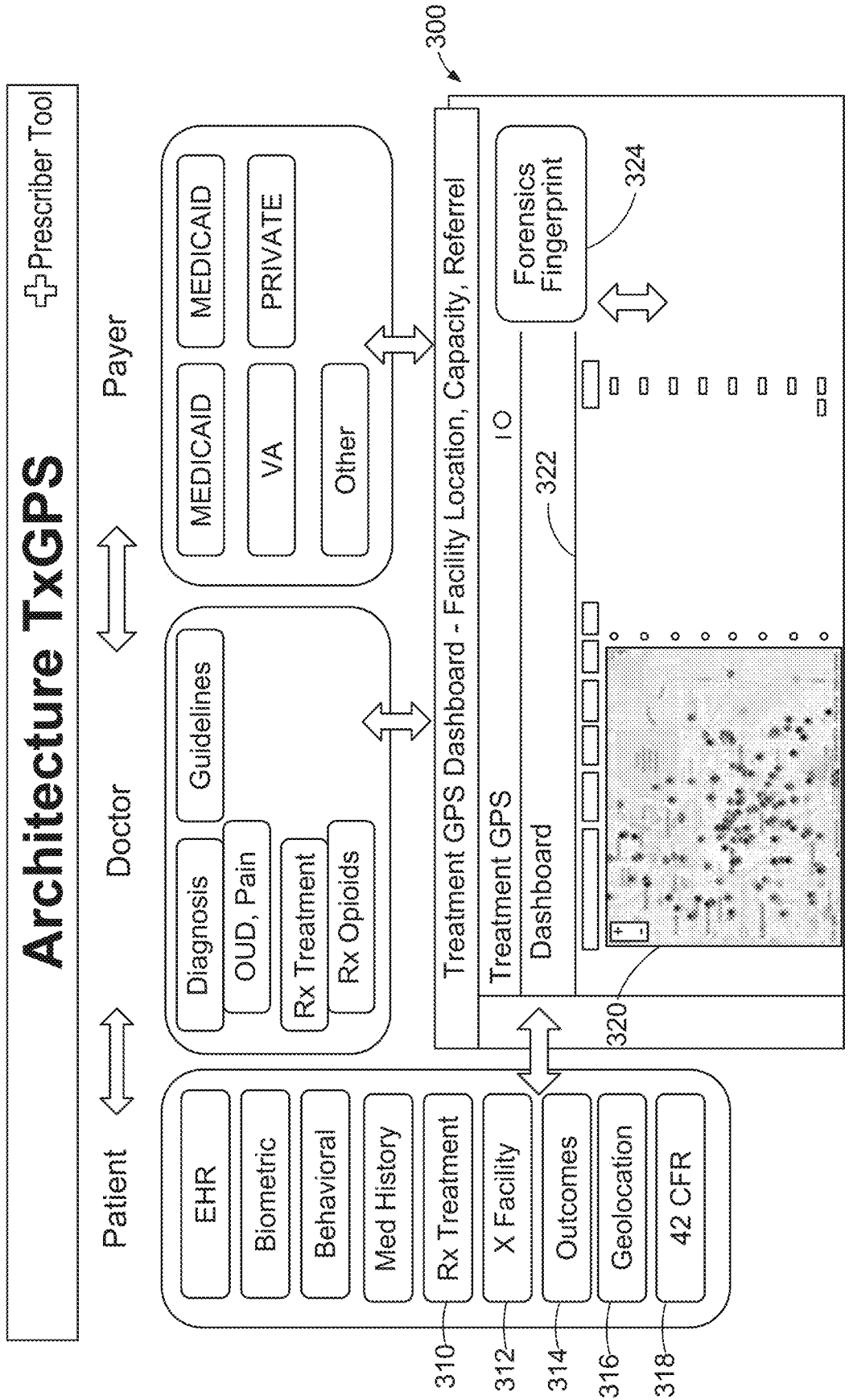
FIG. 3 is a diagram illustrating an example architecture for a referral system, in accordance with an implementation of the present disclosure.

FIG. 3 is a diagram illustrating an example architecture for a referral system 100 implemented with the pharmacological evaluation system 200. The provider module 160 may obtain information from the pharmacological evaluation system 200. The pharmacological evaluation system 200 may be supplemented with provider data records to include, for example, prescription treatments 310, X waiver certifications 312 for a facility, facility outcomes 314, and facility geolocation 316. In an aspect, the pharmacological evaluation system 200 may store a consent form 318 (e.g., in compliance with 42 CFR), for example, within the PPVN.

The referral system 100 may provide a treatment dashboard 300 that presents the results of the provider module 160. The treatment dashboard 300 may include a map 320 that shows the geographic location of one or more providers that have been matched to the patient. The treatment dashboard 300 may include a list 322 that provides information for each of the matched providers. The treatment dashboard 300 may provide a link to a forensics fingerprint 324 that captures the information used to determine the matched providers.

Figure 4:
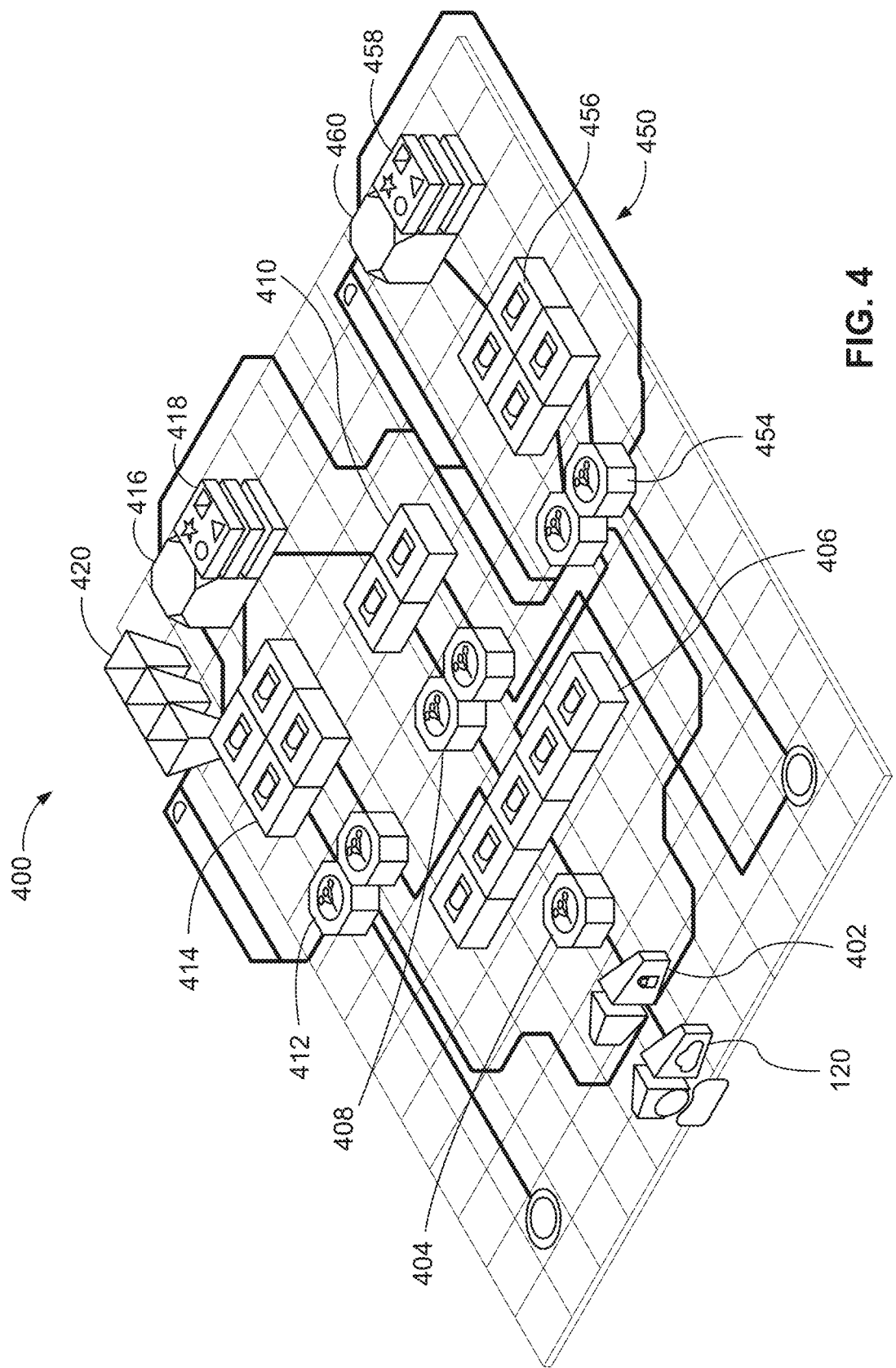
FIG. 4 is a conceptual diagram of an example implementation of a computer system, in accordance with an implementation of the present disclosure.

FIG. 4 illustrates an example of a network or cloud services system 400 for implementing the referral system 100. The system 400 may interact with a PDMP system 450, for example, to acquire data records. A user may access the system 400 via the user device 120, which may contact a cloud gateway 402 that directs the user to a web server 406 via a local backhaul 404. Web server 406 may host the referral system 100 and/or the pharmacological evaluation system 200. The web server 406 may access the PDMP system 450 via an API backhaul 454. The system 400 may include a referral API 410 that provides access to functions of the referral system 100 and a pharmacological evaluation API 414 that provides access to functions of the pharmacological evaluation system 200. The web server 406 may access the referral API 410 via an API backhaul 408 and may access the pharmacological evaluation API 414 via an API backhaul 412. The referral API 410 and the pharmacological evaluation API 414 may access a database 416. Access to the database 416 may be controlled by an access controller 418, which may implement the records component 154. An example implementation of access controller 418 is described below with respect to FIG. 5. A file storage 420 may include a blockchain storage and may implement the PPVN component 158.

The PDMP system 450 may be an example of a patient system 210 that stores patient data. The system 400 may access the PDMP system 450 via API server 456. The PDMP system 450 may include an access controller 458, and a PDMP database 460.

Figure 5:
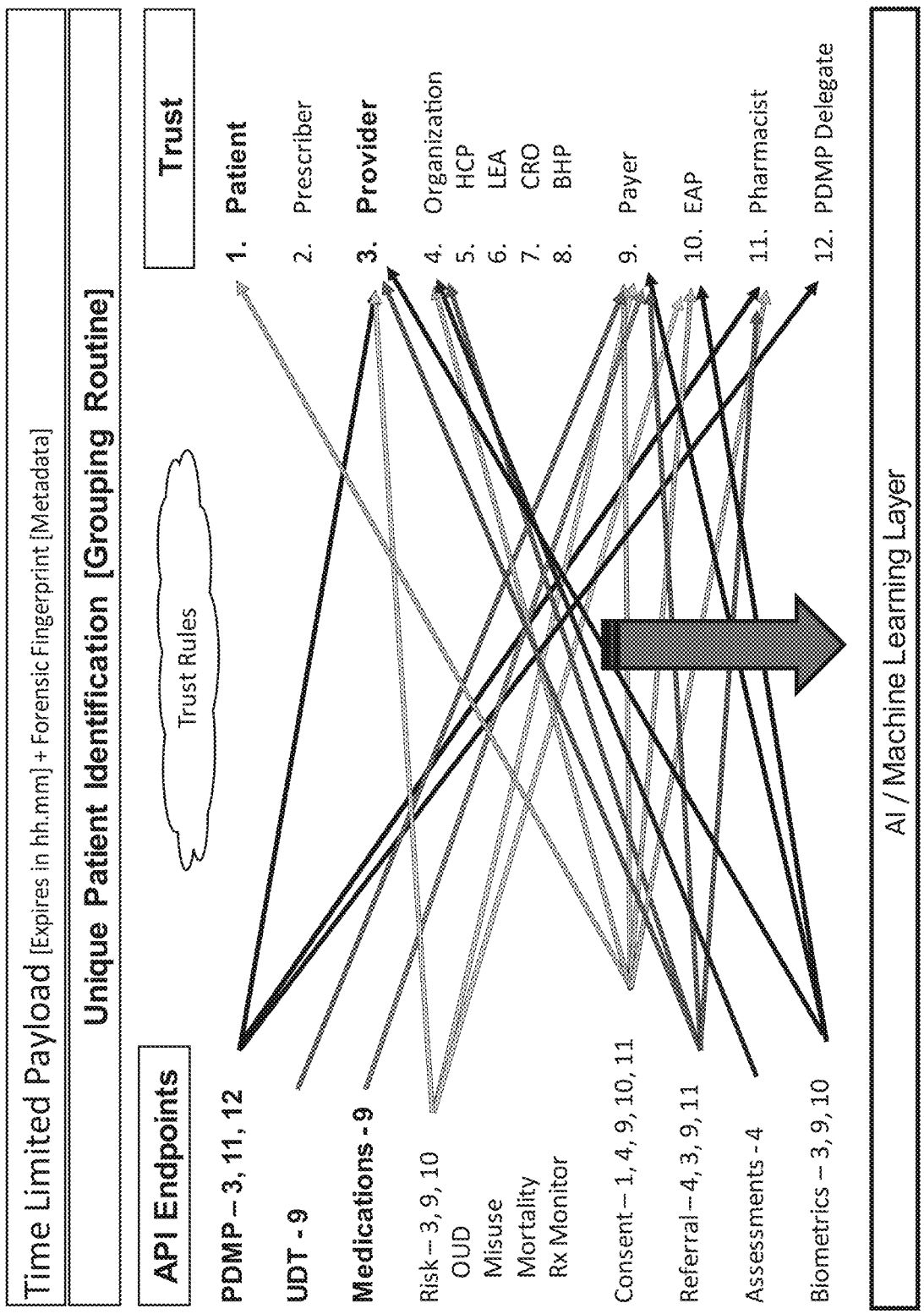
FIG. 5 illustrates example records processing operations, in accordance with an implementation of the present disclosure.

FIG. 5 illustrates an example operation of a records component 154 and/or access controller 418. The records component 154 may generate a time limited payload including a plurality of data records. The time limited payload may have a set expiration time (e.g., when the underlying data is expected to be updated) and a forensic fingerprint. The forensic fingerprint may be a collection of metadata describing the source and timing of the limited time payload.

The records component 154 may identify a unique patient within the data records. For example, data records for a unique patient may use different identification numbers or names within different systems. For example, the records component 154 may identify data records with overlapping elements and conflicting elements. The records component 154 may determine, based on the overlapping elements that the data records are for the same person. The records component 154 may consolidate the data records into a single virtual data record with the conflicting elements represented by a union of the conflicting elements or the conflicting element from a data record with a highest accuracy rating.

The records component 154 may also use trust rules to control the flow of data to various entities. For example, trust rules may define an association between each data source or API endpoint and one or more trusted entities that are allowed to receive data from the API endpoint. The trust rules may be based on contractual (e.g., consent forms) or legal access to certain types of data. When a trusted entity requests an analysis (e.g., by executing one or more machine learning algorithms), the records component 154 may determine whether the data records needed for the particular request are accessible to the entity.

FIG. 6 illustrates an example user interface 600 that may be included in the provider interface 153. The user interface 600 may allow a health care provider operating a treatment center to provide or update a provider record. The user interface 600 may include tabs 610 identifying different functions of the provider interface 153. For example, the tabs 610 may include a provider details tab for entering general information for a provider, a treatment details tab for specifying specific treatments available, a notes tab, a change log tab, and a referrals tab. The treatment details tab is illustrated as an example. The treatment details tab may include a menu 620 including different categories of information related to treatments such as care type, payment type, facility type, treatment approach, service setting, organization type, licensing/accreditation, age coverage, and gender coverage. The treatment details tab may also include a list 630 including individual items and associated checkboxes. Accordingly, for example, the health care provider may specify individual types of care provided.

Figure 7:
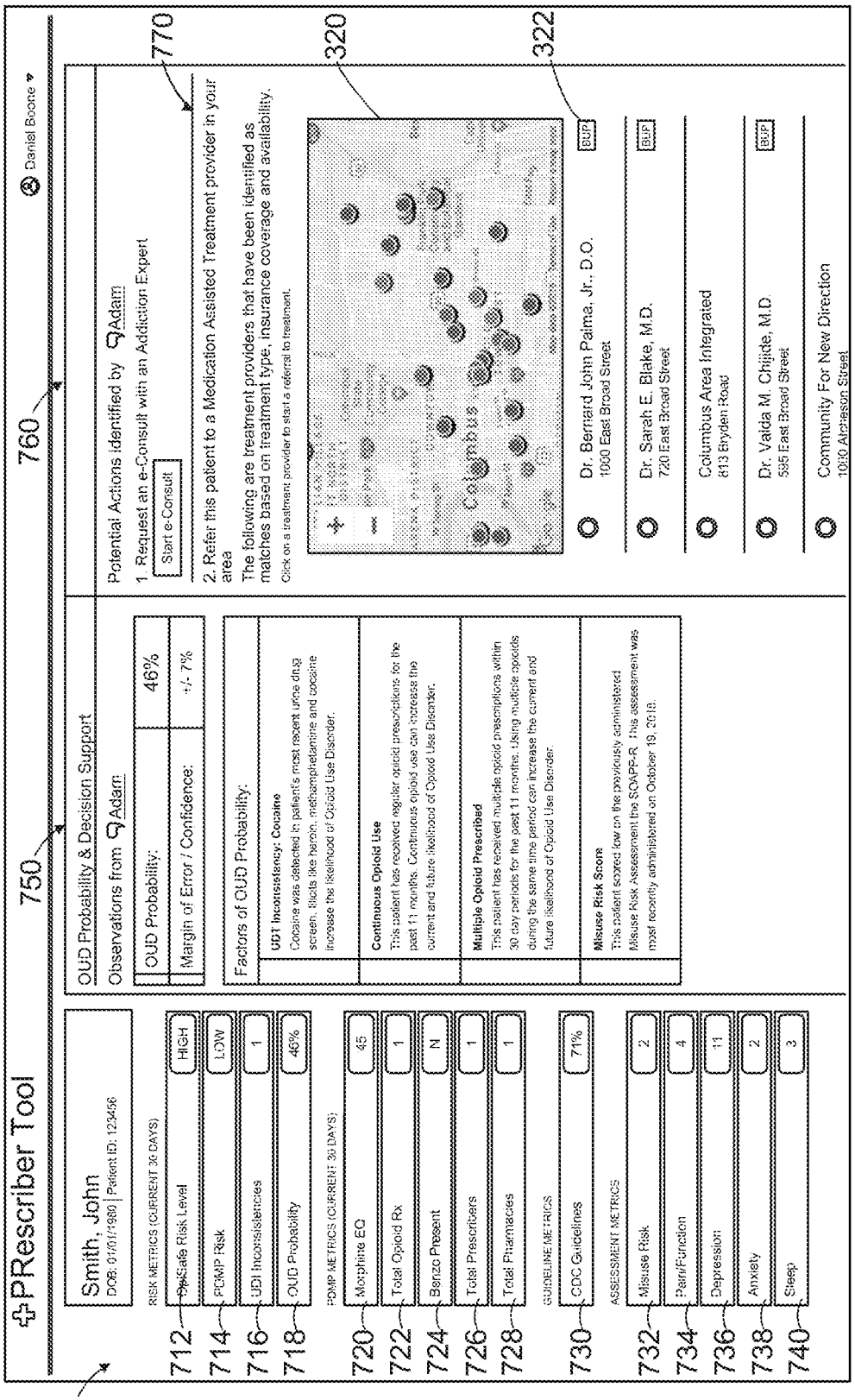
FIG. 7 illustrates an example user interface integrating a referral system into a pharmacological evaluation system, in accordance with an implementation of the present disclosure.

FIG. 7 illustrates an example user interface 700 that may be included in the provider interface 153. The user interface 700 may integrate the referral application 150 into the pharmacological evaluation system 200. For example, the user interface 700 may combine output from the ADAM system and the referral application 150. As illustrated, the user interface 700 may recommend therapeutic treatment information for a patient, generate therapeutic recommendations and guidance for administration of drugs and drug combinations, and/or provide a referral to a health care provider.

In an aspect, the user interface 700 may include a patient information area 710 that includes various metrics for patient for determining a risk of a substance use disorder such as OUD. For example, the metrics may include risk metrics based on a recent monitoring window (e.g., 30 days). Example metrics may include an overall metric 712, a PDMP risk 714, urinary drug test (UDT) inconsistency 716, and OUD probability 718. The PDMP risk 714 may be based on a PDMP metrics, which may include morphine equivalents 720, total prescribed opioids 722, presence of benzodiazepine prescriptions 724, total number of prescribers 726, and total pharmacies 728. A UDT inconsistency 716 may indicate discrepancies between reported drug use and detected drug use. For example, misuse (e.g., too much of a monitored drug detected in blood for written and filled prescriptions; possibly acquiring them from other sources) or diversion (too little of a monitored drug detected in blood based on written and prescriptions—possibly distributing them to other sources) are both examples of inconsistencies. In general, inconsistencies may be detected based on what scripts were written, what scripts were filled, who filled them and when, and what is in the patient's body—urine based on toxicology tests. A guideline metric 730 may be a score based on a published CDC guideline for a condition (e.g., OUD). Assessment metrics may include results from any assessments that the patient has previously performed, for example, for misuse risk 732, pain/function score 734, depression score 736, anxiety score 738, and sleep score 740.

The ADAM system may generate observations 750 including the OUD probability 718 and a margin of error. The observations 750 may also include factors of OUD probability that summarize the risk factors contributing the OUD probability. The risk factors may be color coded to highlight importance.

In an aspect, the ADAM system may recommend potential actions 760 that may be fulfilled using the referral application 150. For example, the referral application 150 may output elements of the treatment dashboard 300 (FIG. 3) in a referral area 770. For example, the referral area 770 may include the map 320 that shows the geographic location of one or more providers that have been matched to the patient and the list 322 that provides information for each of the matched providers.

Figure 8:
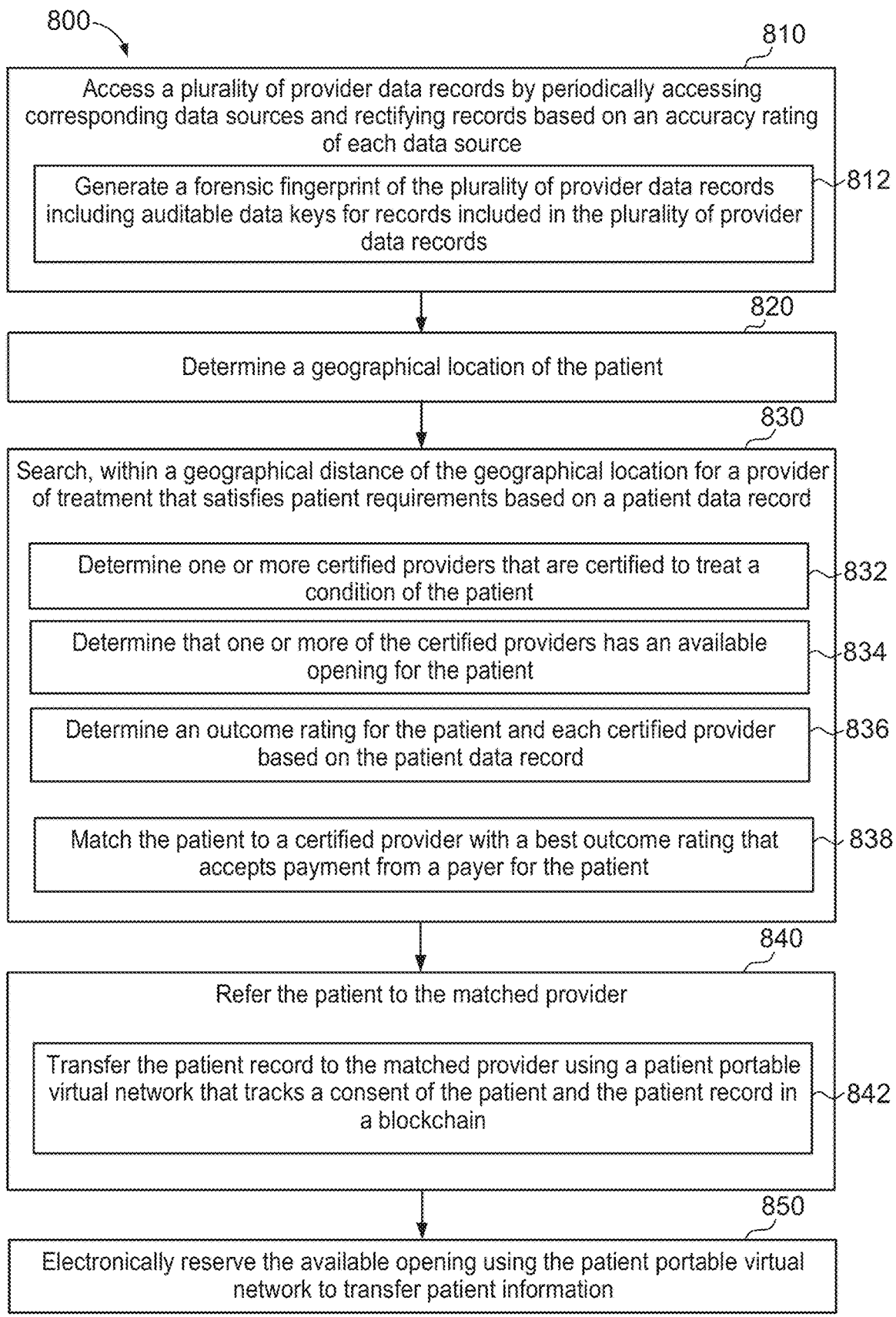
FIG. 8 is a flowchart of an example method of providing a referral to a provider, in accordance with an implementation of the present disclosure.

Turning to FIG. 8, an example method 800 for providing referrals for treatment of opioid use disorder is illustrated. For example, method 800 may be performed by the referral application 150 on the computer device 110.

At block 810, the method 800 may include accessing a plurality of provider data records by periodically accessing corresponding data sources and rectifying records based on an accuracy rating of each data source. In an aspect, for example, the records component 154 may access a plurality of provider data records by periodically accessing corresponding data sources and rectifying records based on an accuracy rating of each data source. At sub-block 812, the block 810 may include generating a forensic fingerprint of the plurality of provider data records including auditable data keys for records included in the plurality of provider data records. For example, the fingerprint component 156 may generate the forensic fingerprint 324 of the plurality of provider data records including auditable data keys for records included in the plurality of provider data records.

At block 820, the method 800 may include determining a geographical location of the patient. In an aspect, for example, the referrer interface 152 and/or the user device 120 may determine the geographical location of the patient. For example, the user may enter the geographical location of the patient via the referrer interface 152 or the user device 120 may determine a GPS location of the patient.

At block 830, the method 800 may include searching, within a geographical distance of the geographical location for a provider that satisfies patient requirements based on a patient data record, wherein the searching includes. In an aspect, for example, the provider module 160 may search, within the geographical distance of the geographical location for one or more providers that satisfy the patient requirements based on the patient record.

At sub-block 832, the block 830 may include determining one or more certified providers that are certified to treat a condition of the patient. In an aspect, the certification component 164 may determine the one or more certified providers that are certified to treat a condition of the patient.

At sub-block 834, the block 830 may include determining that one or more of the certified providers has an available opening for the patient. In an aspect, the availability component 166 may determine that one or more of the certified providers has an available opening for the patient.

At sub-block 836, the block 830 may include determining an outcome rating for the patient and each certified provider based on the patient data record. In an aspect, the rating component 168 may determine an outcome rating for the patient and each certified provider based on the patient data record. In an implementation, the rating component 168 may determine a provider success rate by patient profile and determine a provider success rate with referral provider by patient profile. The rating component 168 may determine the outcome rating based on the success rates. In another implementation, the rating component 168 may determine a similarity between a patient demographic matrix of the provider based on an age, sex, and ethnicity and the patient based on the patient data record. In another implementation, the rating component 168 may utilize a machine learning algorithm (e.g., reinforcement learning based on patient results or feedback) to improve the outcome ratings.

At sub-block 838, the block 830 may include matching the patient to a certified provider with a best outcome rating that accepts payment from a payer for the patient. In an aspect, the provider module 160 may match the patient to a certified provider with a best outcome rating that accepts payment from a payer for the patient.

At block 840, the method 800 may include referring the patient to the matched provider. In an aspect, for example, the reservation component 170 may refer the patient to the matched provider. In an aspect, at sub-block 842, the block 840 may include transferring the patient record to the matched provider using a patient portable virtual network that tracks a consent of the patient and the patient record in a blockchain. For instance, the reservation component 170 may utilize the PPVN component 158 to transfer the patient record to the matched provider.

At block 850, the method 800 may include electronically reserving the available opening using the patient portable virtual network to transfer patient information. For example, the reservation component 170 may electronically reserve the available opening using the PPVN component 158.

Figure 9:
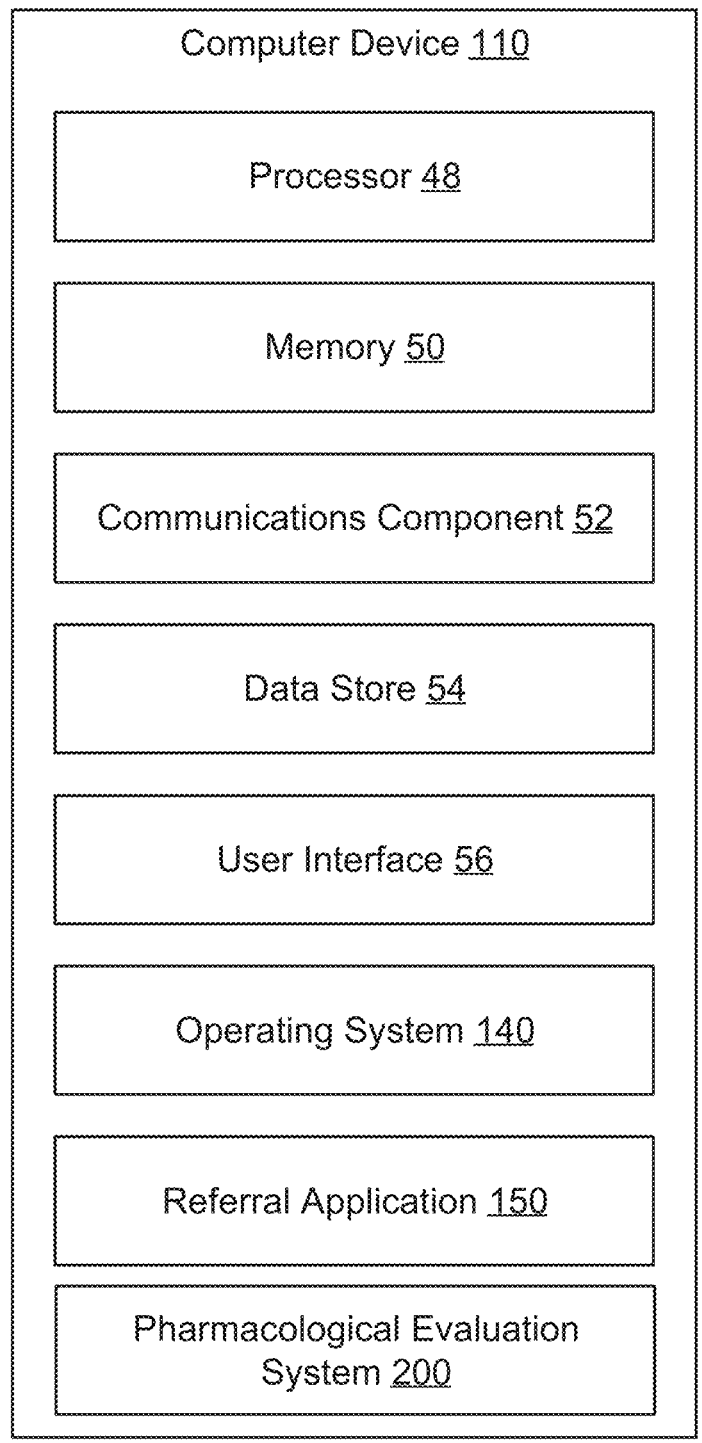
FIG. 9 is a schematic block diagram of an example computer device, in accordance with an implementation of the present disclosure.

Referring now to FIG. 9, illustrated is an example computer device 110 in accordance with an implementation, including additional component details as compared to FIG. 1. In one example, computer device 110 may include processor 48 for carrying out processing functions associated with one or more of components and functions described herein. Processor 48 can include a single or multiple set of processors or multi-core processors. Moreover, processor 48 can be implemented as an integrated processing system and/or a distributed processing system. In an implementation, for example, processor 48 may include CPU 114.

In an example, computer device 110 may include memory 50 for storing instructions executable by the processor 48 for carrying out the functions described herein. In an implementation, for example, memory 50 may include memory 116. The memory 50 may include instructions for executing the referral application 150 and/or the pharmacological evaluation system 200.

Further, computer device 110 may include a communications component 52 that provides for establishing and maintaining communications with one or more parties utilizing hardware, software, and services as described herein. Communications component 52 may carry communications between components on computer device 110, as well as between computer device 110 and external devices, such as devices located across a communications network and/or devices serially or locally connected to computer device 110. For example, communications component 52 may include one or more buses, and may further include transmit chain components and receive chain components associated with a transmitter and receiver, respectively, operable for interfacing with external devices.

Additionally, computer device 110 may include a data store 54, which can be any suitable combination of hardware and/or software, that provides for mass storage of information, databases, and programs employed in connection with implementations described herein. For example, data store 54 may be a data repository for operating system 140 and/or applications 130. The data store may include memory 116 and/or storage device 118.

Computer device 110 may also include a user interface component 56 operable to receive inputs from a user of computer device 110 and further operable to generate outputs for presentation to the user. User interface component 56 may include one or more input devices, including but not limited to a keyboard, a number pad, a mouse, a touch-sensitive display, a digitizer, a navigation key, a function key, a microphone, a voice recognition component, any other mechanism capable of receiving an input from a user, or any combination thereof. Further, user interface component 56 may include one or more output devices, including but not limited to a display, a speaker, a haptic feedback mechanism, a printer, any other mechanism capable of presenting an output to a user, or any combination thereof.

In an implementation, user interface component 56 may transmit and/or receive messages corresponding to the operation of operating system 140 and/or applications 130. In addition, processor 48 may execute operating system 140 and/or applications 130, and memory 50 or data store 54 may store them.

As used in this application, the terms "component," "system" and the like are intended to include a computer-related entity, such as but not limited to hardware, firmware, a combination of hardware and software, software, or software in execution. For example, a component may be, but is not limited to being, a process running on a processor, a processor, an object, an executable, a thread of execution, a program, and/or a computer. By way of illustration, both an application running on a computer device and the computer device can be a component. One or more components can reside within a process and/or thread of execution and a component may be localized on one computer and/or distributed between two or more computers. In addition, these components can execute from various computer readable media having various data structures stored thereon. The components may communicate by way of local and/or remote processes such as in accordance with a signal having one or more data packets, such as data from one component interacting with another component in a local system, distributed system, and/or across a network such as the Internet with other systems by way of the signal.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Various implementations or features may have been presented in terms of systems that may include a number of devices, components, modules, and the like. A person skilled in the art should understand and appreciate that the various systems may include additional devices, components, modules, etc. and/or may not include all of the devices, components, modules etc. discussed in connection with the figures. A combination of these approaches may also be used.

The various illustrative logics, logical blocks, and actions of methods described in connection with the embodiments disclosed herein may be implemented or performed with a specially-programmed one of a general purpose processor, a GPU, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computer devices, e.g., a combination of a DSP and a microprocessor, a plurality of microprocessors, one or more microprocessors in conjunction with a DSP core, or any other such configuration. Additionally, at least one processor may comprise one or more components operable to perform one or more of the steps and/or actions described above.

Further, the steps and/or actions of a method or procedure described in connection with the implementations disclosed herein may be embodied directly in hardware, in a software module executed by a processor, or in a combination of the two. A software module may reside in RAM memory, flash memory, ROM memory, EPROM memory, EEPROM memory, registers, a hard disk, a removable disk, a CD-ROM, or any other form of storage medium known in the art. An exemplary storage medium may be coupled to the processor, such that the processor can read information from, and write information to, the storage medium. In the alternative, the storage medium may be integral to the processor. Further, in some implementations, the processor and the storage medium may reside in an ASIC. Additionally, the ASIC may reside in a user terminal. In the alternative, the processor and the storage medium may reside as discrete components in a user terminal. Additionally, in some implementations, the steps and/or actions of a method or procedure may reside as one or any combination or set of codes and/or instructions on a machine readable medium and/or computer readable medium, which may be incorporated into a computer program product.

In one or more implementations, the functions described may be implemented in hardware, software, firmware, or any combination thereof. If implemented in software, the functions may be stored or transmitted as one or more instructions or code on a computer-readable medium. Computer-readable media includes both computer storage media and communication media including any medium that facilitates transfer of a computer program from one place to another. A storage medium may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and Blu-ray disc where disks usually reproduce data magnetically, while discs usually reproduce data optically with lasers. Combinations of the above should also be included within the scope of computer-readable media.

While implementations of the present disclosure have been described in connection with examples thereof, it will be understood by those skilled in the art that variations and modifications of the implementations described above may be made without departing from the scope hereof. Other implementations will be apparent to those skilled in the art from a consideration of the specification or from a practice in accordance with examples disclosed herein.

What is claimed is:

1. A method of treating a patient for a substance use disorder, comprising:
   accessing, by a central computer device of a referral system including a central processing unit (CPU) and a memory, a plurality of provider data records by periodically accessing corresponding data sources and rectifying records based on an accuracy rating of each data source, wherein accessing a plurality of provider data records by periodically accessing corresponding data sources and rectifying records based on an accuracy rating of each data source comprises:
      generating a time limited payload including the plurality of data records from the corresponding data sources, the time limited payload having a set expiration time when records in the plurality of data records are expected to be updated;
      generating a forensics fingerprint of the time limited payload including auditable data keys describing the corresponding data source and timing of the plurality of provider data records; and
      consolidating the plurality of data records for the patient into a single virtual data record with conflicting elements represented by a union of the conflicting elements or a conflicting element from a data record with a highest accuracy rating;
   determining a geographical location of the patient;
   searching, within a geographical distance of the geographical location for a provider of treatment that satisfies patient requirements based on the single virtual patient data record, wherein the searching includes:
      determining one or more certified providers that are certified to treat a condition of the patient;
      determining that one or more of the certified providers has a currently available opening for the patient according to the rectified provider records;
      determining an outcome rating for the patient and each certified provider based on the patient data record; and
      matching the patient to a certified provider with the currently available opening and a best outcome rating that accepts payment from a payer for the patient; and
   referring the patient to the matched provider, wherein referring the patient to the matched provider comprises transferring the patient record to the matched provider and electronically reserving the currently available opening.

2. The method of claim 1, wherein referring the patient to the matched provider comprises using a patient portable virtual network that tracks a consent of the patient and the patient record in a blockchain.

3. The method of claim 2, wherein the patient portable virtual network further includes a record of referrals and treatment experiences within the blockchain.

4. The method of claim 1, wherein determining the outcome rating for the patient and each certified provider based on the patient data record comprises:
   determining a provider success rate by patient profile; and
   determining a provider success rate with referral provider by patient profile.

5. The method of claim 1, wherein determining the outcome rating for the patient and each certified provider based on the patient data record comprises:
   determining a similarity between a patient demographic matrix of the provider based on an age, sex, and ethnicity and the patient based on the patient data record.

6. A system for treating a patient for a substance use disorder, comprising:
   a memory storing computer-executable instructions; and
   a processor configured to execute the computer-executable instructions to:
   access a plurality of provider data records by periodically accessing corresponding data sources and rectifying records based on an accuracy rating of each data source, wherein to access the plurality of provider data records and rectify records based on an accuracy rating of each data source, the processor is configured to:
      generate a time limited payload including the plurality of data records from the corresponding data sources, the time limited payload having a set expiration time when records in the plurality of data records are expected to be updated;

generate a forensics fingerprint of the time limited payload including auditable data keys describing the corresponding data source and timing of the plurality of provider data records; and consolidate the plurality of data records for the patient into a single virtual data record with conflicting elements represented by a union of the conflicting elements or a conflicting element from a data record with a highest accuracy rating;

determine a geographical location of the patient;

search, within a geographical distance of the geographical location for a provider of treatment that satisfies patient requirements based on the single virtual patient data record;

determine one or more certified providers that are certified to treat a condition of the patient;

determine that one or more of the certified providers has a currently available opening for the patient according to the rectified provider records;

determine an outcome rating for the patient and each certified provider based on the patient data record;

match the patient to a certified provider with the currently available opening and a best outcome rating that accepts payment from a payer for the patient; and refer the patient to the matched provider by transferring the patient record to the matched provider and electronically reserving the currently available opening.

7. The system of claim 6, wherein the processor is configured to execute the instructions to transfer the patient record to the matched provider using a patient portable virtual network that tracks a consent of the patient and the single virtual patient record in a blockchain.

8. The system of claim 7, wherein the patient portable virtual network further includes a record of referrals and treatment experiences within the blockchain.

9. The system of claim 6, wherein the processor is configured to execute the instructions to:
determine a provider success rate by patient profile; and
determine a provider success rate with referral provider by patient profile.

10. The system of claim 6, wherein the processor is configured to execute the instructions to determine a similarity between a patient demographic matrix of the provider based on an age, sex, and ethnicity and the patient based on the patient data record.

11. A non-transitory computer readable medium storing computer-executable instructions that when executed by a processor cause the processor to:

access a plurality of provider data records by periodically accessing corresponding data sources and rectifying records based on an accuracy rating of each data source, wherein the instructions to access the plurality of provider data records and rectify records based on an accuracy rating of each data source, include instructions to:

generate a time limited payload including the plurality of data records from the corresponding data sources, the time limited payload having a set expiration time when records in the plurality of data records are expected to be updated;

generate a forensics fingerprint of the time limited payload including auditable data keys describing the corresponding data source and timing of the plurality of provider data records; and consolidate the plurality of data records for a patient into a single virtual data record with conflicting elements represented by a union of conflicting elements or a conflicting element from a data record with a highest accuracy rating;

determine a geographical location of a patient;

search, within a geographical distance of the geographical location for a provider of treatment that satisfies patient requirements based on the single virtual patient data record;

determine one or more certified providers that are certified to treat a condition of the patient;

determine that one or more of the certified providers has a currently available opening for the patient according to the rectified provider records;

determine an outcome rating for the patient and each certified provider based on the patient data record;

match the patient to a certified provider with the currently available opening and a best outcome rating that accepts payment from a payer for the patient; and refer the patient to the matched provider by transferring the patient record to the matched provider and electronically reserving the currently available opening.

* * * * *